(12) United States Patent
Chakradhar

(10) Patent No.: US 11,845,982 B2
(45) Date of Patent: Dec. 19, 2023

(54) KEY-VALUE STORE THAT HARNESSES LIVE MICRO-ORGANISMS TO STORE AND RETRIEVE DIGITAL INFORMATION

(71) Applicant: Anjali Chakradhar, Manalapan, NJ (US)

(72) Inventor: Anjali Chakradhar, Manalapan, NJ (US)

( * ) Notice: Subject to any disclaimer, the term of this patent is extended or adjusted under 35 U.S.C. 154(b) by 1696 days.

(21) Appl. No.: 15/855,294

(22) Filed: Dec. 27, 2017

(65) Prior Publication Data

US 2019/0194738 A1     Jun. 27, 2019

(51) Int. Cl.
| | | |
|---|---|---|
| C12Q 1/6869 | (2018.01) | |
| C12Q 1/6876 | (2018.01) | |
| C12N 15/10 | (2006.01) | |
| G01N 15/14 | (2006.01) | |
| G01N 21/64 | (2006.01) | |
| G16B 50/00 | (2019.01) | |

(52) U.S. Cl.
CPC ....... *C12Q 1/6869* (2013.01); *C12N 15/1086* (2013.01); *C12N 15/1089* (2013.01); *C12Q 1/6876* (2013.01); *G01N 15/1429* (2013.01); *G01N 15/1434* (2013.01); *G01N 21/6428* (2013.01); *G01N 2015/149* (2013.01); *G01N 2021/6439* (2013.01); *G16B 50/00* (2019.02)

(58) Field of Classification Search
CPC ................ C12Q 1/6869; C12Q 1/6876; C12N 15/1086; G01N 15/1429; G01N 15/1434; G01N 21/6428
See application file for complete search history.

(56) References Cited

PUBLICATIONS

Nguyen et al. "Long-Term Stability and Integrity of Plasmid-Based DNA Data Storage," Polymers (Jan. 2018) vol. 10, No. 28, pp. 1-10. (Year: 2018).*
Bonnet et al. "Rewritable Digital Data Storage in Live Cells via Engineered Control of Recombination Directionality" PNAS (2012) vol. 109, No. 23, pp. 8884-8889 (Year: 2012).*
Kim et al. "Simultaneous Sorting of Multiple Bacterial Targets Using Integrated Dielectrophoretic-Magnetic Activated Cell Sorter" Lap Chip (2009) vol. 9, pp. 2313-2318 (Year: 2009).*

* cited by examiner

*Primary Examiner* — Jerry Lin
(74) *Attorney, Agent, or Firm* — Sughrue Mion, PLLC

(57) ABSTRACT

A digital store comprising of a method to store digital data in live micro-organisms, and a method to selectively retrieve subsets of stored data, is disclosed. Digital data is represented as a plurality of key-value pairs. The proposed system stores copies of key-value pairs in a plurality of live micro-organisms. Upon presentation of a retrieval key, the proposed digital store retrieves the value associated with the retrieval key. Storage method for a key-value pair comprises of (a) mapping the key to a gene that expresses a unique fluorescent protein so that no two keys map to the same gene, (b) encoding the key-value pair as base-pair sequences, (c) synthesizing oligonucleotide chains from base-pairs for the key-value pair and the gene, (d) synthesizing recombinant DNA plasmids that have oligonucleotide chains for the key-value pair, the gene, and two primers, as foreign DNA inserts, (e) incorporation of recombinant DNA plasmids into live micro-organisms, (f) isolation of live micro-organisms that have absorbed the recombinant DNA plasmids, and (g) safe storage of population of live micro-organisms with embedded key-value pairs in a common pool. Retrieval of the value paired with a key comprises of (a) taking as input the retrieval key, and mapping the key to the specific gene for fluorescent protein, (b) taking a sample from the safe storage pool that contains live micro-organisms embedded with key-value pairs, (c) isolating the live micro-organisms that have expressed the gene by using high-speed fluorescence activated cell sorting or flow cytometry, (d) extracting DNA from the recombinant DNA plasmid in the isolated live micro-organisms, (d) selectively amplifying and sequencing only those DNA strands that contain the value for the key, and (e) decoding the base-pair sequence obtained after DNA sequencing to yield the value associated with the retrieval key.

We also disclose two important variations. The first variation relates to the storage step. The recombinant DNA plasmid is constructed to include additional non-fluorescent oligonucleotides and genes so that during the data retrieval step, the live micro-organisms that have absorbed the said plasmid can be sorted by cell sorters based on parameters of individual cells such as cell size, cell complexity, cell phenotype, cell structure, cell function, and magnetic or electrical properties. The second variation relates to both storage and retrieval of key-value pairs with large values. To store such a key-value pair, the large value is split into smaller blocks so that a block can fit into a recombinant DNA plasmid, and a distinct pair of primers is used for each block. A block's primer pair is used to selectively amplify and sequence only the DNA that encodes the data in the block, thereby enabling the retrieval of a specific block of the value, as opposed to retrieving the entire value associated with a key.

16 Claims, 3 Drawing Sheets

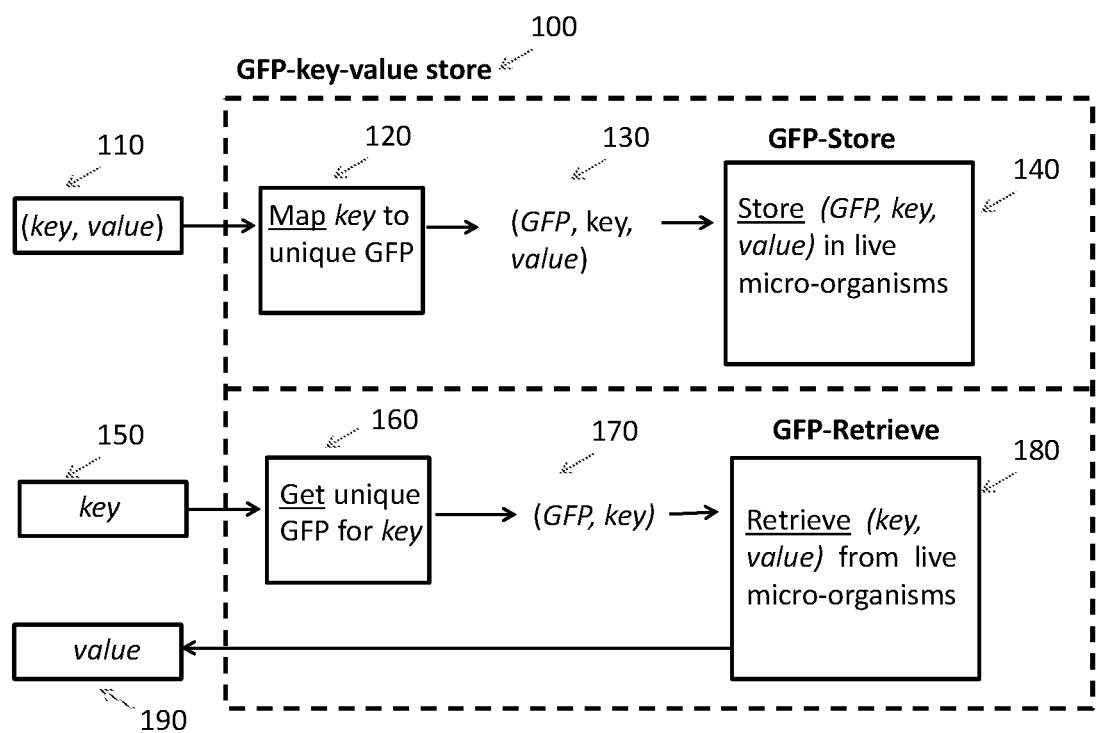
Figure 1: A digital storage system that harnesses live micro-organisms

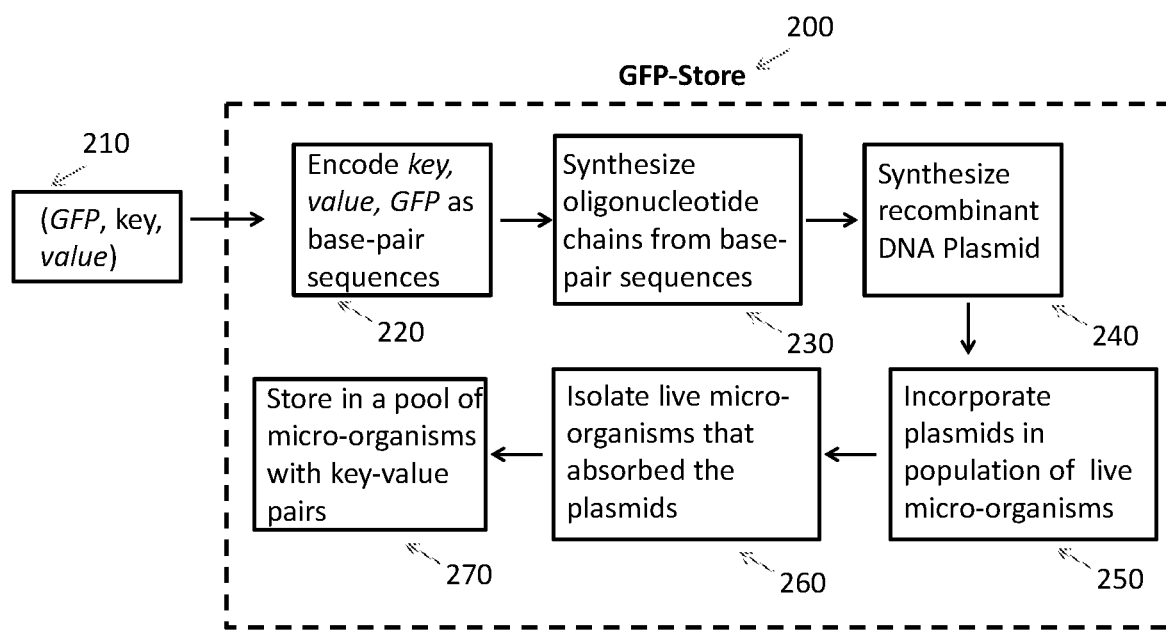
Figure 2: A procedure to store a key-value pair in live micro-organisms

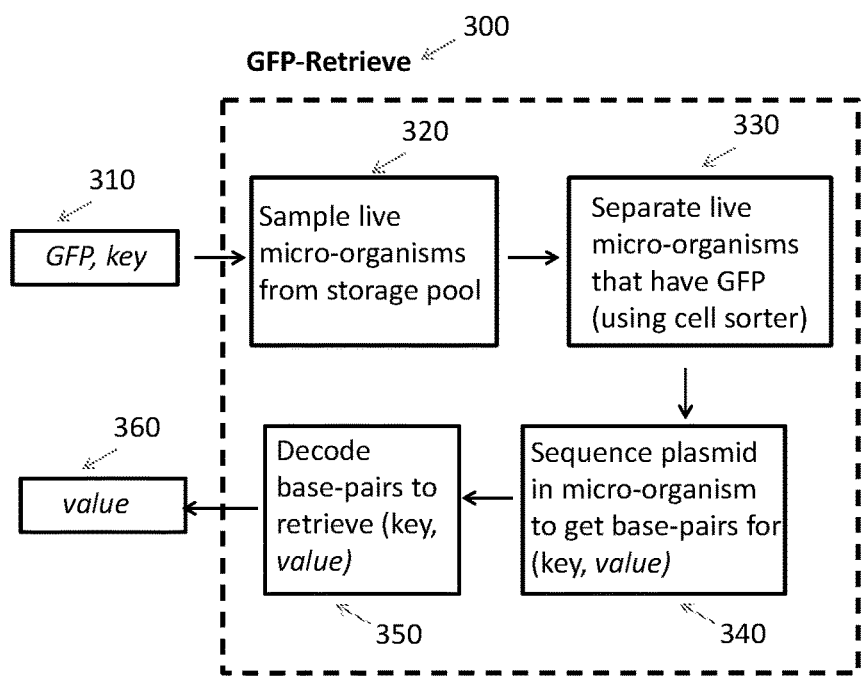
Figure 3: A procedure to retrieve a key-value pair from live micro-organisms

KEY-VALUE STORE THAT HARNESSES LIVE MICRO-ORGANISMS TO STORE AND RETRIEVE DIGITAL INFORMATION

BACKGROUND

1. Field

This invention relates to a method of information storage and retrieval that harnesses biological processes in live micro-organisms and genetic engineering to store and retrieve digital data.

2. Description of the Related Art

Humanity has generated more archived data in the past two years than in all of preceding history, and soon, hard drives may not be able to store it all. DNA sequences can be a potential medium for digital storage. DNA storage methods [1] store digital data in the base sequence of the DNA. To retrieve data, DNA is sequenced to obtain the base sequence, and the base pairs are decoded to yield digital data. DNA storage is significant for several reasons. DNA is the highest-density large-scale data storage scheme ever invented –215 petabytes can be stored in a single gram of DNA [1]. It is remarkably easy to reliably duplicate DNA in large quantities through methods like PCR [1]. DNA can survive in cold, dry, or dark conditions for thousands of years. Arguably most importantly, DNA will not become obsolete as long as there are DNA-based living organisms.

There are two radically different types of DNA storage methods: in-vitro DNA storage, and in-vivo DNA storage.

In-vitro (i.e. taking place in a test-tube, culture dish or elsewhere outside of any living organism) DNA storage methods use artificial DNA made using commercially available oligonucleotide synthesis machines for storage and DNA sequencing machines for retrieval of base sequence in the artificial DNA. These methods use naked synthetic DNA strands, typically floating within tubes of liquid. Several in-vitro DNA storage methods have been reported recently [2][3][4][5]. However, in-vitro DNA storage is expensive ($7K to store 2 MB, and $2K to read the stored data [3]) but advances in oligonucleotide synthesis and gene sequencing are expected to bring 10,000-fold reduction in cost. Also, almost all known in-vitro DNA storage methods cannot selectively retrieve subsets of stored data, which analytics algorithms require to mine insights from big data. To read even a single byte from the DNA storage, the entire DNA pool of strands must be sequenced and decoded. To address this limitation, researchers at University of Washington reported a method [5] in April 2016 to sequence and decode only a subset of the synthetic DNA to retrieve any data set out of several data sets stored in the DNA storage system.

In sharp contrast to in-vitro methods, in-vivo (i.e. taking place inside a living organism) DNA storage methods harness live micro-organisms, and these methods can dramatically lower the costs of storage. Unlike naked synthetic DNA strands in a test tube, live micro-organisms multiply. Therefore, the data in these organisms does not degrade, and the organisms pass on this customized information to the next generation, making this form of biological data storage extremely efficient and powerful. However, storing data in live micro-organisms requires radically different techniques than schemes used by in-vitro stores. This is because the artificial DNA sequences with data may not be stable in-vivo, and such sequences may adversely interfere with the normal genetic and biological mechanisms in live micro-organisms. In July 2017, researchers at Harvard University exploited the CRISPR-based adaptive-immunity mechanism in prokaryotes to store practical amounts of data in genomes of living bacteria [6]. To retrieve data, they extract DNA from different bacteria in the population and sequence their entire genomes. Nucleotide sequence obtained from DNA sequencing are decoded to yield the digital information stored within the genome of living bacteria.

Our invention applies to in-vivo storage and retrieval of digital data.

Unfortunately, all prior in-vivo DNA storage methods suffer from a serious drawback: they all have the disadvantage that the whole DNA in the population of the living micro-organisms has to be sequenced to retrieve one of several data sets that were previously stored in the population. In other words, none of the prior in-vivo methods provide random-access (i.e. selective access) to just one of the many data sets encoded in the population. A mechanism to directly access and retrieve a select subset of data remarkably improves the data retrieval time in in-vivo methods.

Unlike all prior in-vivo DNA storage methods, our DNA digital storage invention discloses a radically new method to store digital data in live micro-organisms, and our unique storage method enables a new retrieval method that selectively retrieves random subsets of the stored data.

SUMMARY

As our invention, we propose a radically new method to store digital data as DNA in live micro-organisms, and our unique storage method enables a new retrieval method that selectively retrieves random subsets of the data stored in live micro-organisms. Our method can be used to store and retrieve a variety of digital data like text, images, video and audio data.

Storing digital data in live micro-organisms, as proposed in our invention, has several advantages. Unlike methods that store digital data as base sequence in naked synthetic DNA strands in a test tube, live micro-organisms multiply. Therefore, the data in these organisms does not degrade, and the organisms pass on this customized information to the next generation, making this form of biological data storage extremely efficient and powerful. These advantages also dramatically lower the costs of storage.

Unlike all prior methods that harness live micro-organisms to store data, our invention discloses a new method to selectively retrieve subsets of the data stored in live micro-organisms. This is in sharp contrast to prior methods that require the retrieval of the entire data stored in the population of the live micro-organisms, even if only a subset of the stored data is required. Such selective retrieval of only the desired subset of data not only shortens the retrieval time by orders of magnitude, but it is also a fundamental capability that is necessary for big data analytics to mine valuable insights from the large amounts of data that can be stored in live micro-organisms.

We envision the use of our invention by the world's most wealthy and powerful corporations like Facebook, Apple, Google, and the US government. They are all making astounding investments in magnetic digital storage, but humanity has generated more archived data in the past two years than in all of preceding history, and soon, hard drives may not be able to store it all. Acknowledging this inevitability, these corporations are all now investing in the prospect of storing information in digital DNA stores.

These and other features and advantages will become apparent from the following detailed description of illustrative embodiments thereof, which is to be read in connection with the accompanying drawings.

BRIEF DESCRIPTION OF THE DRAWINGS

The disclosure will provide details in the following description of preferred embodiments with reference to the following figures wherein:

FIG. 1 shows the overall block diagram of the proposed system to store and selectively retrieve digital information in live micro-organisms.

FIG. 2 shows the preferred embodiment of a process to store digital information as key-value pairs in a population of live micro-organisms.

FIG. 3 shows the preferred embodiment of a process to retrieve the value in a key-value pair, upon presentation of the key.

DETAILED DESCRIPTION OF THE PREFERRED EMBODIMENTS

Key-value store: Digital information is represented as a collection of records, which in turn can have many different fields within them. Each record is a value, and these records are stored and retrieved using a key that uniquely identifies the record. A key-value pair consists of a record and a key that uniquely identifies the record. A key-value store is a data storage scheme for storing and retrieving key-value pairs. Given a key, a key-value store can quickly retrieve the value. This type of data structure is also known as dictionary or hash.

Overview of proposed DNA digital store: FIG. 1 shows an overview of the proposed DNA digital store. Given a key-value pair 110, the key is mapped to a unique gene that expresses a fluorescent protein (GFP). The mapping of keys to GFPs is maintained in a two-column table 120. This mapping ensures that every key is mapped to a unique GFP. The combination of GFP, key and value 130 is presented to the GFP-Store 140, which stores the key-value pair in live micro-organisms. To retrieve information, a key 150 is given as input to the digital store. The key is mapped to its corresponding GFP by using the two-column table 160 that contains the mapping of keys to GFPs. Subsequently, the GFP and the key 170 are used by the GFP-Retrieve method 180 to retrieve the key-value 190 pair from live micro-organisms.

Storage method: FIG. 2 shows the procedure to store a key-value pair. Given a combination of GFP, key and value 210, the encoding method 220 encodes the GFP, key and value into three separate base-pair sequences. These three base-pair sequences are synthesized 230 into three oligo-nucleotide chains, or artificial DNA strands, which are subsequently included in the synthesis 240 of a recombinant DNA plasmid. A plurality of recombinant plasmids is incorporated 250 into a population of live micro-organisms that do not have a recombinant DNA plasmid, or any gene that expresses a fluorescent protein. Since only a few of the live micro-organisms typically absorb the recombinant DNA plasmids, such organisms are isolated 260 from the rest of the micro-organisms that have not absorbed the plasmids. Live micro-organisms with the recombinant DNA plasmid in their cells are stored in a common pool 270 with micro-organisms that store other key-value pairs.

Encoding data as base-pairs: Digital data is represented as a sequence of two symbols 0 and 1. Naturally occurring DNA consists of four types of nucleotides: adenine (A), thymine (T), cytosine (C) and guanine (G). The two symbols 0 and 1 can be mapped to the four symbols A, T, C and G in many ways. As an example, the symbol 0 can be mapped to the combination AT and the symbol 1 can be mapped to the combination GC. Then, a binary sequence like 101 can be represented as a nucleotide sequence GCATGC. A comparison of various encoding methods that have been used by DNA stores is available in [7]. Methods that encode digital data as a sequence of base-pairs typically trade off encoding density for more reliable manufacturing of oligonucleotides. It is also common to use error-correction schemes, and different nucleotide sequences to encode the same data, because such redundancy helps offset errors that are invariably introduced in oligonucleotide synthesis and DNA sequencing. Data could be lost during evolution, and a preferred encoding for storage of data in live micro-organisms is described in [6].

Manufacture of base-pairs as artificial DNA: Rapid advances in solid phase-based synthesis technologies have made automated high-throughput custom oligonucleotide chains possible [8]. Oligonucleotide chains are made by using a DNA synthesizer, which is a computer-controlled reagent delivery system. The first base is attached to a solid support, usually a glass or polystyrene bead, and the first base anchors the growing DNA chain of bases in the reaction column. Appropriate nucleotides are sequentially coupled to the growing oligonucleotide chain in the order required by the base-pair sequence. Two points are worth noting about oligonucleotide synthesis. There is a practical limit on the length of oligonucleotide chain (about 200 nucleotides) because the number of errors in assembling the chain increase with the length of the chain. Coupling efficiency, a measure of how efficiently the DNA synthesizer is adding new bases to the growing DNA chain, is around 99%. This means that DNA synthesizer makes mistakes as often as 1 in every 100 nucleotides. To account for these errors, methods that encode digital data as base-pairs introduce significant amount of redundancy in encoding.

Synthesis of recombinant DNA plasmid: Plasmids are small circular double-stranded pieces of DNA that replicate independently from the chromosomal DNA of the host. Natural plasmids are mostly found in prokaryotes, and range in size from a few thousand base pairs to more than 100,000 base pairs. Like the host-cell chromosomal DNA, plasmid DNA is duplicated before every cell division and a copy is segregated to each daughter cell. This assures continued propagation of the plasmid through successive generations of the host cell.

Plasmids are also routinely synthesized in the laboratory for DNA cloning [8], where foreign DNA is injected into live micro-organisms for duplication. Artificial plasmids typically include recombinant DNA, which is any DNA molecule formed by joining DNA fragments from different sources. The ease of modifying plasmids and the ability of plasmids to self-replicate within a cell make them attractive tools for biotechnology scientists and genetic engineers. To simplify working with artificial plasmids, their size is typically restricted to 3000 base pairs. In the present invention, we engineer the design of the plasmid to achieve the following objectives, and we illustrate ways to achieve these objectives:

a) Duplication: After a plasmid is absorbed into a live micro-organism, replication of the plasmid (along with replication of the host cell) is essential to assure propagation of the key-value pair embedded in the plasmid through successive generations of the host cell. This can be achieved as follows. Every plasmid has an origin of replication (ORI), which is a specific DNA sequence of 50-100 base pairs that must be present in a plasmid for it to replicate. Host-cell enzymes bind to ORI, initiating replication of the circular plasmid. After DNA replication is initiated at ORI, it continues around the circular plasmid regardless of the nucleotide sequence. Therefore, any DNA sequence inserted into such a plasmid is replicated along with the rest of the plasmid DNA, and this property is exploited by the present invention to store and assure continued propagation through successive generations of the host cell.

b) Isolation: After plasmids are absorbed into a population of live micro-organisms, it is necessary to separate micro-organisms that have absorbed a plasmid from the rest of the population. This can be achieved as follows. The selectable marker region of a plasmid allows placement of one or more selection markers (they are also specific DNA sequences). These markers enable isolation of plasmid-containing live micro-organisms. As an example, if we add an antibiotic resistance gene [10] in the selectable marker region, then live micro-organisms that have absorbed the plasmid will express this gene and resist antibiotics, while the rest die when exposed to the antibiotic.

c) Cell-sortability: After a unique plasmid is created for every key-value pair, micro-organisms that absorb plasmids embedded with key-value pairs co-exist in a common pool. However, during the retrieval method, it is necessary to quickly separate live micro-organisms that contain a specific key-value pair that corresponds to the given retrieval key. To enable cell-sorting, we engineer the plasmid to include a cell-sorting metric that a high-speed fluorescence activated cell sorter can use to classify and separate micro-organisms. As an example of a cell-sorting metric, in the present invention every key is mapped to a unique gene responsible for synthesis of a specific fluorescent protein, and the said gene is inserted into the plasmid. After the said plasmid is absorbed by live micro-organisms, the expression of the said gene results in a fluorescent protein. A fluorescence activated cell sorter detects the said fluorescent protein, and isolates the live micro-organisms that have the said fluorescent protein. Insertion of genes that express proteins into a plasmid requires additional care. A plasmid has multiple sites where new DNA sequences can be inserted. These are the restriction sites, which are also specific DNA sequences, that allow for easy insertion of foreign DNA. Molecular scissors called restriction enzymes are used to cut plasmids open at the restriction sites, and new DNA sequences are inserted into the cut plasmid. The resulting DNA fragments from different sources are joined together by DNA ligase. This allows scientists to cut and paste components of plasmid together. The restriction sites are often downstream from a promoter, which is yet another specific DNA sequence of about 100 to a 1000 base pairs. Promoter [10] is important because it drives the transcription of genes inserted at the restriction sites. The sequence of the promoter region controls the binding of the RNA polymerase and transcription factors, and promoters play a large role in determining where and when a gene of interest will be expressed. Promoter also determines which cell types the gene is expressed in and how much recombinant protein is produced by the gene (host transcription machinery varies across different types of live micro-organisms). As an illustration, to store a key-value pair in a plasmid, the said key's gene for fluorescent protein can be inserted at a restriction site that is downstream from the promoter, and the gene expression can be controlled by appropriate choice of the promoter sequence.

d) Payload insertion: Artificial DNA sequences corresponding to a key and value are also inserted at the restriction sites, but transcription of these sequences into proteins is inhibited through promoter regulation [10].

e) Amplification: After a cell-sorter isolates live micro-organisms that contain a specific key-value pair, DNA sequencing determines the sequence of base-pairs in the recombinant DNA plasmid. Prior to DNA sequencing, PCR is a common technique that is used in the laboratory to make millions of copies of (i.e. amplify) a particular section of DNA, starting from a very small amount of DNA. However, short stretches of DNA called the primers are necessary to initiate the PCR reaction, and two primers have to flank the section of DNA to be amplified on either side. Therefore, during the synthesis of the recombinant DNA plasmid, two primers are added to flank the payload (key-value pair) on either side.

Electroporation into live micro-organisms: Transformation process facilitates absorption of recombinant DNA plasmids by live micro-organisms [12, 13]. Transformation of bacteria with plasmids is important because bacteria are used as the means for both storing and replicating plasmids. Therefore, nearly all artificial plasmids routinely carry a bacterial origin of replication. Also, specific treatments have been discovered that make bacteria more susceptible to either chemical or electrical based transformation, and such treatments generate 'competent cells.' Many companies sell competent cells, which come frozen and are prepared for optimal transformation efficiencies upon thawing. The two popular methods of bacterial transformation are heat shock of chemically prepared competent cells (chemical transformation), and electroporation of competent cells. Chemically competent cells absorb small plasmids fast and are easy to use, but such cells are less efficient at taking up larger plasmids. To transform large plasmids with key-value pairs, it is better to use electro-competent cells. Instead of relying on the heat-shock to cause the cells to take up the recombinant DNA plasmid, an electro-magnetic field is applied to the cell/DNA mixture to induce membrane permeability [14], and such electroporation is an order of magnitude more efficient than chemical transformation.

Isolation of micro-organisms that absorbed the plasmid: Isolation is easily accomplished by adding an antibiotic resistance gene [11] in the selectable marker region of the recombinant DNA plasmid. Then, live micro-organisms that have absorbed the plasmid will express this gene and exhibit resistance to antibiotics, while the rest die when exposed to the antibiotic.

Retrieval method: FIG. 3 shows the procedure 300 to retrieve a key-value pair. Given a combination of the retrieval key and its GFP 310, a sample is taken 320 from the storage pool that has a population of live micro-organisms with different key-value pairs. A fluorescence activated cell sorter 330 separates live micro-organisms in the sample that have expressed the protein corresponding to the GFP gene. Subsequently, recombinant plasmid DNA is extracted from these micro-organisms, and DNA sequencing 340 determines the base-pair sequence in the recombinant DNA. This base pair sequence is then decoded 350 to yield the value (digital data) 360 that corresponds to the retrieval key.

Cell sorting: Micro-organisms that absorbed plasmids embedded with key-value pairs co-exist in a common pool. However, during the retrieval method, it is necessary to quickly separate live micro-organisms that contain a specific key-value pair that corresponds to the given retrieval key. Since the plasmids in the micro-organisms are expressing fluorescent proteins, it is possible to separate the micro-organisms with a desired fluorescent protein by using cell sorters. Fluorescence-activated cell sorting (FACS) [16] is a specialized type of flow cytometry [15]. It provides a fast, objective and quantitative recording of fluorescent signals from individual cells. This enables sorting a heterogeneous mixture of biological cells into two or more containers, one cell at a time, based upon the specific light scattering and fluorescent characteristics of each living cell. Cell sorters can also sort based on one or more (cell-sortability) properties of the cell like cell size, complexity, phenotype or structure, and magnetic or electrical characteristics. This capability can be exploited by designing the recombinant DNA plasmid to include suitable cell-sortability metrics.

DNA sequencing of recombinant DNA plasmid: Many methods have been developed to purify plasmid DNA from bacteria [17]. These methods involve three steps: growth of the bacterial culture, harvesting and lysis of the bacteria, and purification of plasmid DNA. DNA sequencing determines the sequence of base-pairs in the purified recombinant DNA plasmid. Prior to DNA sequencing, PCR is a is used in the laboratory to make millions of copies of (i.e. amplify) of the payload section (key-value pair) of the recombinant DNA plasmid, starting from a very small amount of DNA. The primers necessary to initiate the PCR reaction already flank the section of DNA to be amplified on either side (this was done during the synthesis of the recombinant DNA plasmid). After PCR, known methods [18] can be employed to sequence the payload section of the recombinant DNA.

Decoding of base-pairs of payload section to reveal value: Decoding of base-pairs depends on the encoding used during the storage method. As an example, if the symbol 0 was mapped to the combination AT and the symbol 1 was mapped to the combination GC during encoding, then a base pair sequence GCATGC is decoded as the binary sequence 101.

Having described preferred embodiments of a system and method for an in-vivo digital DNA store that stores data in live micro-organisms, and retrieves selective subsets of stored data (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

What is claimed is:

1. A digital storage and retrieval method, consisting of a method to store digital data in living micro-organisms, comprising of:
   (a) representing data as one or more key-value pairs,
   (b) mapping a key in a key-value pair to a gene that expresses a unique fluorescent protein so that no two keys map to the same fluorescent gene,
   (c) synthesizing the sequence of base-pairs of the said fluorescent gene as the first oligonucleotide chain,
   (d) encoding the said key and the key's value as a sequence of base-pairs, and synthesizing the base-pair sequence as the second oligonucleotide chain,
   (e) synthesizing a recombinant DNA plasmid by including the first and second oligonucleotide chains,
   (f) incorporating the said recombinant DNA plasmid into live micro-organisms that do not have a fluorescent gene or a recombinant plasmid in their cells,
   (g) selecting micro-organisms that have successfully absorbed the said recombinant DNA plasmid, and
   (h) storing the said micro-organisms separately or in a pool with other micro-organisms that are storing key-value pairs, and, a method to retrieve data stored in live micro-organisms, comprising of:
   (a) taking as input the retrieval key, which is the key of a key-value pair to be retrieved from data stored in live micro-organisms,
   (b) determining the fluorescent gene associated with the retrieval key,
   (c) taking a sample of live micro-organisms that store different key-value pairs, and separating the live micro-organisms that have expressed the said fluorescent gene by employing high-speed fluorescence cell sorting or flow cytometry,
   (d) sequencing the genome of the recombinant DNA plasmid in the said micro-organisms that were isolated through cell sorting, and
   (e) decoding the base-pairs obtained after genome sequencing of the recombinant DNA plasmid to recover the value corresponding to retrieval key.

2. The method of claim 1, wherein the storage method maps a key to a multiplicity of genes, each of which expresses a different fluorescent protein, and no two keys are mapped to the same combination of genes.

3. The method of claim 2, wherein the retrieval method separates micro-organisms that express fluorescent proteins corresponding to the multiplicity of genes mapped to the retrieval key by using fluorescence activated cell sorters.

4. The method of claim 1, wherein the storage method maps a key to a combination of one or more fluorescent genes and one or more properties of the cell.

5. The method of claim 4, wherein the retrieval method separates micro-organisms based on fluorescent proteins and one or more properties of the cell.

6. The method of claim 1, wherein the storage method maps a key to also include a pool number so that micro-organisms with key-value pairs can be stored in different pools that are indexed by the pool number, rather than having all micro-organisms in a single pool.

7. The method of claim 6, wherein the retrieval method takes a sample of live micro-organisms only from a specific pool whose pool number corresponds to the pool number in the retrieval key.

8. The method of claim 1, wherein the storage method includes addition of an antibiotic-resistance gene in the recombinant DNA plasmid.

9. The method of claim 8, wherein the storage method selects micro-organisms that show resistance to the said antibiotic to be the micro-organisms that have successfully absorbed a recombinant DNA plasmid into their cell.

10. The method of claim 1, wherein the storage method includes addition of two primers in the recombinant DNA plasmid, and these primers flank the base-pairs sequence that corresponds to the value of the key-value pair to be stored.

11. The method of claim 10, wherein the retrieval method uses the primers added to the recombinant DNA plasmid to amplify the base-pairs sequence that corresponds to the value associated with the retrieval key, and facilitate DNA sequencing of the DNA strands that contain desired base-pairs.

12. The method of claim 1, wherein the retrieval method separates the live micro-organisms by using magnetic cell sorting.

13. The method of claim 1, wherein the storage method stores a large value in a group of live organisms, comprising of:
- (a) breaking up the value of a key-value pair into smaller blocks of data so that every block of data fits within one recombinant DNA plasmid,
- (b) assigning a unique block number to each block of data,
- (c) adding a header to each block of data, and the said header includes total number of blocks for the said value, and the block number for the said block of data, and
- (d) encoding the said header and the said block of data as a sequence of base-pairs (which are synthesized into an oligonucleotide chain that is included in a recombinant DNA plasmid), and
- (e) synthesizing as many recombinant DNA plasmids as there are blocks of data.

14. The method of claim 13, wherein retrieval of a large value associated with a particular key, comprises of:
- (a) sequencing a recombinant DNA plasmid that contains the said key to retrieve a block of data,
- (b) reading the total number of blocks, and the block number from the retrieved block of data, and
- (c) continuing sequencing of recombinant DNA plasmids until all blocks of data that comprise the said value are retrieved.

15. A digital storage and retrieval system, consisting of a sub-system to store digital data in living micro-organisms, comprising of:
- (a) a unit to represent data as one or more key-value pairs,
- (b) a unit to map a key in a key-value pair to a gene that expresses a unique fluorescent protein so that no two keys map to the same fluorescent gene,
- (c) a unit to synthesize the sequence of base-pairs of the said fluorescent gene as the first oligonucleotide chain,
- (d) a unit to encode the said key's value as a sequence of base-pairs, and a unit to synthesize the base-pair sequence as the second oligonucleotide chain,
- (e) a unit to synthesize a recombinant DNA plasmid by including the first and second oligonucleotide chains,
- (f) a unit to incorporate the said recombinant DNA plasmid into live micro-organisms that do not have a fluorescent gene or a recombinant plasmid in their cells,
- (g) a unit to select micro-organisms that have successfully absorbed the said recombinant DNA plasmid into their cell, and
- (h) a unit to store the said micro-organisms separately or in a pool with other micro-organisms that are storing key-value pairs, and, a sub-system to retrieve data stored in live micro-organisms, comprising of:
- (i) a unit to take as input the retrieval key, which is the key of a key-value pair to be retrieved from data stored in live micro-organisms,
- (j) a unit to determine the fluorescent gene associated with the retrieval key,
- (k) a unit to take a sample of live micro-organisms that store different key-value pairs, and another unit to separate the live micro-organisms that have expressed the said fluorescent gene by employing high-speed fluorescence cell sorting or flow cytometry,
- (l) a unit to sequence the DNA of the recombinant DNA plasmid in the said micro-organisms that were isolated through cell sorting, and
- (m) a unit to decode the base-pairs obtained after genome sequencing of the recombinant DNA plasmid to recover the value corresponding to retrieval key.

16. A computer program product including a tangible computer readable medium with instructions, said instructions enabling a computer to store and retrieve digital data, consisting of instructions to store digital data in living micro-organisms, and said instructions comprising:
- (a) representing data as one or more key-value pairs,
- (b) mapping a key in a key-value pair to a gene that expresses a unique fluorescent protein so that no two keys map to the same fluorescent gene,
- (c) synthesizing the sequence of base-pairs of the said fluorescent gene as the first oligonucleotide chain,
- (d) encoding the said key's value as a sequence of base-pairs, and synthesizing the base-pair sequence as the second oligonucleotide chain,
- (e) synthesizing a recombinant DNA plasmid by including the first and second oligonucleotide chains,
- (f) incorporating the said recombinant DNA plasmid into live micro-organisms that do not have a fluorescent gene or a recombinant plasmid in their cells,
- (g) selecting micro-organisms that have successfully absorbed the said recombinant DNA plasmid into their cell, and
- (h) storing the said micro-organisms separately or in a pool with other micro-organisms that are storing key-value pairs, and, consisting of instructions to retrieve data stored in live micro-organisms, and said instructions comprising of:
- (i) taking as input the retrieval key, which is the key of a key-value pair to be retrieved from data stored in live micro-organisms,
- (j) determining the fluorescent gene associated with the retrieval key,
- (k) taking a sample of live micro-organisms that store different key-value pairs, and separating the live micro-organisms that have expressed the said fluorescent gene by employing high-speed fluorescence cell sorting or flow cytometry,
- (l) sequencing the genome of the recombinant DNA plasmid in the said micro-organisms that were isolated through cell sorting, and
- (m) decoding the base-pairs obtained after genome sequencing of the recombinant DNA plasmid to recover the value corresponding to retrieval key.

\* \* \* \* \*